United States Patent [19]

af Ekenstam et al.

[11] 4,214,049
[45] Jul. 22, 1980

[54] ASSAY OF SERINE PROTEASES USING NOVEL CHROMOGENIC ENZYME SUBSTRATES

[75] Inventors: Bo T. af Ekenstam, Mölndal; Leif E. Aurell; Karl G. Claeson, both of Särö; Birgitta G. Karlsson; Stig I. Gustavsson, both of Mölndal; Gun A. Olausson, Västra Frölunda, all of Sweden

[73] Assignee: AB Kabi, Stockholm, Sweden

[21] Appl. No.: 955,441

[22] Filed: Oct. 27, 1978

Related U.S. Application Data

[60] Division of Ser. No. 888,586, Mar. 20, 1978, Pat. No. 4,137,225, which is a continuation of Ser. No. 697,002, Jun. 17, 1976, abandoned.

[30] Foreign Application Priority Data

Jul. 11, 1975 [SE] Sweden ................................ 7507974

[51] Int. Cl.² .............................................. G01N 31/14
[52] U.S. Cl. ...................................................... 435/23
[58] Field of Search .................................. 435/23, 24; 195/103.5 R

[56] References Cited

U.S. PATENT DOCUMENTS

| 3,884,896 | 5/1975 | Blomback et al. | 435/24 |
| 4,016,042 | 5/1977 | Svendsen | 435/23 |
| 4,070,245 | 1/1978 | Svendsen | 435/23 |

*Primary Examiner*—Esther M. Kepplinger
*Attorney, Agent, or Firm*—Pollock, Vande Sande & Priddy

[57] ABSTRACT

Method for the quantitative determination of serine proteases which includes contacting the substance for which the determination is desired with a diagnostically active chromogenic substrate with good stability and high specificity to serine proteases having the formula: H—D—$A_1$—$A_2$—$A_3$—NH—R or salts thereof, wherein $A_1$ is Gly, Ala, Val, Leu, Ile, Pip, Pro, or Aze; $A_2$ is Gly, Ala, Val, Leu, Ile, Pip, Pro, Aze, or Phe; $A_3$ is Arg, Lys, or Orn, and R is a chromophoric group.

31 Claims, No Drawings

ASSAY OF SERINE PROTEASES USING NOVEL CHROMOGENIC ENZYME SUBSTRATES

This is a division of application Ser. No. 888,586 filed Mar. 20, 1978, now U.S. Pat. No. 4,137,225, which in turn is a continuation of application Ser. No. 697,002 filed June 17, 1976 and now abandoned.

The present invention relates to novel chromogenic substrates for enzymes of the type serine proteases (EC 3.4.21). The substrates according to the invention are especially suitable for quantitative determination of the above-classified enzymes, which split in the peptide chain on the carboxyl side of arginine or lysine. Further the substrates can be used for a study of reactions in which the said enzymes are formed, inhibited or consumed, or for determination of factors influencing or taking part in such a reaction. Synthetical substrates for enzyme-determination have great advantages as compared to the natural ones, provided that they fulfil certain conditions, such as a great sensitivity for and specificity for the enzyme, a good solubility in water or the biological test liquid and an easy detectibility of some of the splitting products.

Excellent substrates for the determination of e.g. plasmin, thrombin, trypsin, kallikrein and urokinase are inter alia described in the Swedish Pat. No. 380.258 and are in principle chromogenic tripeptide derivatives. Among the best substrates of this type are those having a benzoylated N-terminal end and a chromophoric group coupled to the C-terminal end, e.g.:

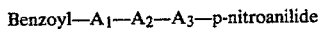

Benzoyl—A$_1$—A$_2$—A$_3$—p-nitroanilide        I wherein A$_1$, A$_2$, A$_3$ are amino acids.

With specific amino acid sequences it is possible to among the said substrates obtain such with a special sensitivity for a certain or certain enzymes. Upon enzymatic hydrolysis the substrates form the chromophoric product p-nitroaniline which easily can be determined spectrophotometrically. These substrates have, however, a delimitation due to their relatively low solubility ($\leq$1 mg/ml). A slow solubility necessitates work very near the saturation limit for the substrates for achieving a satisfactory substrate concentration. In enzyme determinations in different biological systems it may thus occur that either the substrate per se is precipitated or a combination of protein/substrate. The said precipitations cause erroneous spectrophotometer readings and thus erroneous enzyme determinations.

The benzoylated enzyme substrates according to type I become considerably more soluble if the N-terminal benzoyl group is replaced with H. The now free protonized amino group of the amino acid A$_1$ increases the solubility but causes also, however, that the rate with which the enzyme splits the substrates decreases (cf. Table II). Further, the substrates can now in a biological test solution in a non-desired way be decomposed from the N-terminal end by amino peptidases.

According to the present invention it has quite unexpectedly been found that if in a substrate according to formula I, which is satisfactory from the activity point of view for a certain enzyme, exchanges the benzoyl group to H and simultaneously replaces the hitherto used L-form of the amino acid A$_1$(L-A$_1$) with its D-form(D-A$_1$) the substrate so obtained will be very easily soluble as expected, but the activity of the substrate in relation to the enzyme does not decrease by the introduction of a D-amino acid but is quite surprisingly several times better than that of the corresponding substrate with solely L-amino acids and often even considerably better than that of the benzoylated good starting substrate according to formula I. The N-terminal free D-amino acid in the new substrate also prevents a non-desired attack by amino peptidases since the said are specific for L-amino acids.

The novel chromogenic substrates according to the invention are characterized by the following general formula:

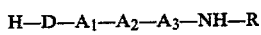

H—D—A$_1$—A$_2$—A$_3$—NH—R or salts thereof, wherein A$_1$ and A$_2$ are chosen among the amino acids Gly, Ala, Val, Leu, Ile, Pip, Pro, Aze, A$_2$ further can be Phe, A$_3$ is chosen among Arg, Lys and Orn, R is chosen among nitrophenyl, naphthyl, nitronaphthyl, metoxynaphthyl, quinolyl and nitroquinolyl (as regards abbreviations cf. page 4).

For the synthesis of the novel chromogenic enzyme substrates conventional protective groups and coupling methods are used, all of which are wellknown within the peptide chemistry.

As the $\alpha$-amino protective group it is of advantage to use carbobenzoxy or t-butyloxy carbonyl or some group related thereto such as for instance p-metoxy, p-nitro or p-metoxyphenylazo-carbobenzoxy.

It is of advantage to use protonization, the groups NO$_2$ or p-toluene sulfonyl for protection of the $\delta$-guanido group of the arginyl group.

As protection for the $\delta$-amino group in ornithine and for the $\epsilon$-amino group in lysine it is of advantage to use above all the groups carbobenzoxy, t-butyloxy carbonyl or p-toluene sulfonyl.

As splittable $\alpha$-carboxy protective group it is suitable to use methyl, ethyl or benzyl ester.

The coupling between two amino acids or a dipeptide and an amino acid is achieved by activation of the $\alpha$-carboxy group. The activated derivative can either be isolated or generated in situ and can be for instance p-nitrophenyl, trichloro phenyl, pentachloro phenyl, N-hydroxy succinimide or N-hydroxy benzotriazole ester, symmetric or asymmetric anhydride or acid azid.

The activation to the above-mentioned ester derivative is with advantage achieved by the presence of a carbodiimide, e.g. N,N'-dicyclo hexylcarbodiimide, which also can serve as activating coupling reagent directly between the carboxy and amine components.

The principle for the substrate synthesis can be stepwise addition of the amino acids to the C-terminal arginyl group, which is either from the beginning provided with a coupled chromophoric group which then acts as a carboxy protective group or provided with a splittable carboxy protective group, and the chromophoric group is then coupled to the protected tripeptide derivative, or alternatively it is in principle possible to choose to synthetize the N-terminal dipeptide fragment per se which subsequently is coupled to the arginyl group with or without a chromophoric group in principle as discussed above.

Independent of the principle chosen a purification of the intermediary and end products by gel filtration chromatography is suitable since this method enables a rapid synthesis work and gives maximal yields.

The invention is described in more detail in the following non-limiting specific examples.

ABBREVIATIONS

Amino acids (if not otherwise stated the L-form is meant):
Arg=Arginine
Aze=2-Azetidine carboxylic acid
Ala=Alanine
Gly=Glycine
Ile=Isoleucine
Leu=Leucine
Lys=Lysine
Phe=Phenyl alanine
Pip=Pipecolinic acid
Pro=Proline
Val=Valine
AcOH=Acetic acid
Bz=Benzoyl
Cbo-=Carbobenzoxy-
DCCI=Dicyclohexyl carbodiimide
DMF=Dimethyl formamide
Et$_3$N=Triethyl amine
EtOAc=Ethyl acetate
GPC=Gel filtration chromatography
HBT=N-hydroxy benzotriazole
HMPTA=N,N,N',N',N'',N''-hexamethyl phosphoric acid triamide
HONSu=N-hydroxy succinimide
MeOH=Methanol
-OpNP=p-nitrophenoxy
-pNA=p-nitroanilide
tBoc=t-butyloxy carbonyl
TFA=Trifluoro acetic acid
TLC=Thin-layer chromatography

REACTION TYPES USED FOR THE SYNTHESIS

For synthesis of the novel enzyme substrates enumerated in Table II the different reaction steps are performed largely in a similar manner. For this reason a general description of the different reaction types is given and subsequently, in Table I, a report of intermediary and end products, the working-up methods used for different reaction types and certain physical data.

REACTION TYPE 1

Coupling of the chromophoric group (R)

20 mmol N$^\alpha$, N$^G$-protected arginine or N$^\alpha$, N$^\omega$-protected ornithine or lysine or in a corresponding manner suitably protected peptide derivative, ground and well-dried, is dissolved in 50 ml of dry freshly distilled HMPTA at room temperature, whereupon 20 mmol Et$_3$N and 30 mmol of the chromophoric amine in the form of its isocyanate derivative is added under moisture-free conditions and under stirring. After one day of reaction time the reaction solution is poured down into 0.5 l of 2% sodium bicarbonate solution under stirring. The precipitation obtained is removed by filtration and washed well with bicarbonate solution, water, 0.5 N hydrochloric acid and water again. From the precipitation the desired product is extracted with e.g. methanol, certain by-products not being dissolved. The methanol extract can, after evaporation, be brought to crystallization from a suitable medium or purified by GPC.

REACTION TYPE 2

Splitting-off a carbobenzoxy protective group (Cbo-)

10 mmol of the well-dried Cbo-derivative is slurried in 25 ml of dry AcOH and 15 ml of 5.6 N HBr in AcOH are added under moisture-free conditions at room temperature. After a reaction time of 45–60 min the solution is fed drop by drop into 300 ml of dry ether with vivid agitation. The ether phase is sucked from the precipitation obtained which is washed with 2-3 portions of 100 ml of ether. The so obtained hydrobromide of N$^\alpha$-deblocked compound is dried over NaOH-tablets in vacuum at 40° C. for 3–16 h.

REACTION TYPE 3

Splitting-off of a t-butyloxy carbonyl protective group (tBoc-)

10 mmol of the well-dried tBoc-derivative are dissolved in 200 ml of 25% TFA in CH$_2$Cl$_2$ under moisture-free conditions at room temperature. After a reaction time of 20 min the solution is fed drop by drop into 500 ml of dry ether. The precipitation obtained is removed by filtration and washed freely with ether. The trifluoro acetate of N$^\alpha$-deblocked compound so obtained is dried over NaOH-tablets under vacuum at 30° C. for 2–3 h.

REACTION TYPE 4

Coupling reactions

Liberation of the α-amino group

For acylation of the derivatives obtained in the reaction types 2 or 3 the α-amino group must be present as a free base. The liberation can be performed in many different ways. Inter alia it is possible to add one equivalent of a dry tertiary amine (e.g. Et$_3$N or N-ethyl morpholine) to a DMF-solution of the HBr or TFA derivative cooled down to −10° C. In cases comprising Et$_3$N and HBr derivatives the precipitated Et$_3$N.HBr is removed by filtration. Alternatively, the HBr or TFA derivative may be dissolved in 5% sodium bicarbonate solution from which the liberated derivative is extracted by e.g. EtOAc or butanol, whereupon the organic phase is dried and evaporated.

(a) with N$^\alpha$-protected active ester derivative.

To a solution of 10 mmol peptide or amino acid derivative liberated according to the above, in 20–50 ml of freshly distilled DMF 11 mmol of N$^\alpha$-protected p-nitrophenyl or N-hydroxy succinimide ester derivative of the amino acid to be coupled on are added at −10° C. After a reaction time of 1 h at −10° C., the solution is buffered with 5 mmol of tertiary amine and is then allowed to slowly adjust to room temperature. The reaction course is suitably followed by TLC-analysis. If required further 5 mmol of base is added after a new cooling. When the reaction is finished the solution is evaporated on a rotavapor to an oily residue which is stirred with a couple of portions of water. The residue is purified by GPC or recrystallization. When GPC is used for purification of the coupling product and this has an eluation volume which wholly or partly coincides with that for the active ester derivative of the coupled amino acid the contamination of the coupling product can be avoided if, after finished reaction but before the evaporation, unconsumed active ester derivative is replaced with an excess (3-5 mmol) of a primary amine, e.g. n-butyl amine, during 30 min at room temperature. Thereafter working-up is performed as described above.

(b) with N$^\alpha$-protected amino acid or peptide and generation of active ester in situ.

To a solution of 10 mmol of the above-mentioned liberated peptide or amino acid derivative in 20–50 ml of freshly distilled DMF 11 mmol of $N^\alpha$-protected amino acid or in a corresponding way protected peptide derivative with a C-terminal free carboxy group, 11 mmol of HBT or HONSu and 11 mmol of DCCI are added at $-10°$ C. After 1–3 h at $-10°$ C. the reaction solution is allowed to adjust to room temperature. The reaction course is suitably followed by TLC-analysis. After finished reaction the solution is poured under stirring down into 100–300 ml of 5% $NaHCO_3$ (aq).

The precipitation obtained is washed with water after filtration or decantation. The residue is purified by GPC or recrystallization.

REACTION TYPE 5

Splitting-off of all protecting groups and purification and ion exchange 0.2–1.0 mmol of the protected peptide derivative with the desired chromophoric group is deprotected by reaction with 5–20 ml of dry HF in the presence of 0.2–1.0 ml of anisole in an apparatus according to Sakakibara, intended for this purpose, during 60 min at 0° C. After finished reaction and after all of the HF has been distilled the raw product is dissolved in 33% aqueous AcOH and purified by GPC. The product is isolated by freeze-drying from diluted AcOH and is submitted to ion exchange on a column consisting of a weakly basic ion exchange resin Sephadex$^{(R)}$ QAE-25 in the chloride form, swollen in MeOH:water, 95:5, with the same medium as dissolution and eluation medium. The pure product is freeze-dried from water.

GEL FILTRATION CHROMATOGRAPHY

By GPC of protected peptide or amino acid derivatives, raw products or evaporated mother lyes after crystallization a simplified working-up procedure and optimal yields are obtained. The substance is then dissolved in MeOH and transferred to a column of a suitable size (volume 0.5–7.5 l, length 100 cm), packed with Sephadex$^{(R)}$ LH-20, swollen in MeOH and eluated with the same solvent. The eluate is fractionated in suitable partial volumes and its UV-absorption (254 nm) is continually determined. Product-containing part fractions are checked for purity by TLC and the pure ones are combined and evaporated.

For purification of peptide derivatives after deprotection with HF according to 5 above the 30% AcOH (aq) solution of the raw product is transferred to a column of a suitable size (volume 0.5–2.0 l, length 60 cm), packed with Sephadex$^{(R)}$ G-15, swollen in 30% aqueous AcOH and eluated with the same solvent. After proceeding according to the above the product-containing pure part fractions are freeze-dried, optionally after a partial evaporation on a rotavapor at 25° C.

THIN-LAYER CHROMATOGRAPHY

For the TLC-analysis preprepared glass plates with "Kiselgel $F_{254}$" (Merck) are used as absorption agents. The solvent systems used (volume ratios) are:

| A: | n-butanol: | AcOH: water | (3:2:1) |
|---|---|---|---|
| $P_1$: | Chloroform: | MeOH | (9:1) |
| $P_{\frac{1}{2}}$: | Chloroform: | MeOH | (19:1) |

After finished chromatography the plate is studied in UV-light (254 nm) and developed with Cl/o-toluidine reagent according to common practice. The stated $R_f$-values are the results from separate chromatographies.

DETERMINATION OF SERINE PROTEASES BY CHROMOGENIC SUBSTRATES

The substrates prepared according to the examples above are used for determination of different enzymes according to the procedure outlined above.

The principle for the determination is based on the fact that the splitting product formed by enzymatic hydrolysis has a UV-spectrum which is essentially different from that of the substrate. Thus, e.g. all p-nitro anilide substrates according to the invention have absorption maxima around 310 nm with the molar extinction coefficient of about 12000. At 405 nm the absorption of these substrates has almost completely discontinued. p-Nitroaniline which has been split off from the substrate during the enzymatic hydrolysis has an absorption maximum at 380 nm and a molar extinction coefficient of 13200, which at 405 nm only has decreased to 9620. By spectrophotometric determination at 405 nm it is thus easy to follow the amount of p-nitroaniline formed which is proportional to the degree of the enzymatic hydrolysis which in its turn is determined by the active amount of enzyme. Table II shows a comparison of relative reaction rates between previously known substrates according to the formula I, their non-benzoylated forms and substrates according to the invention. This table clearly shows the superiority of the substrates according to the invention.

Accordingly, substrates according to the invention are several times better than corresponding substrates with N-terminal L-amino acid and further at least as good as the previously known best substrates which are the benzoylated substrates according to formula I. Further, the greater solubility of the novel substrates (ca 20–300 times greater) is a very great advantage for enzyme determinations above all in biological systems, in which the poor solubility of previously known substrates caused difficult problems, partly due to the fact that substrate saturation could not be achieved and partly due to the risk for undesired precipitations.

The gel Sephadex$^{(R)}$ G-15 used for the gel filtration is a crosslinked dextran gel. The gel Sephadex$^{(R)}$ LH-20 is a hydroxypropylated crosslinked dextran gel. The ion exchanger Sephadex$^{(R)}$ QAE-25 used is a crosslinked dextran gel with diethyl-(2-hydroxy-propyl)-aminoethyl as functional group. These gels are from Pharmacia Fine Chemicals, Uppsala, Sweden.

Table I

| Product | No. | Starting material | Synthesis acc. to reac. type | Yield (%) | Working-up | $[\alpha]_D^{24x}$ |
|---|---|---|---|---|---|---|
| Cbo—Arg($NO_2$)-pNA | I | Cbo—Arg($NO_2$)—OH p-$NO_2$—phenylisocyanate | 1 | 63 | GPC | +20.5(D) |
| tBoc—Lys(Cbo)-pNA | II | tBoc—Lys(Cbo)-pNA | 1 | 67 | Cryst. | −8.5(M) |

Table I-continued

| | | | | | | |
|---|---|---|---|---|---|---|
| | | p-NO$_2$—phenylisocyanate | | | | (EtOH) |
| Cbo—Pro—Arg(NO$_2$)-pNA | III | I, Cbo—Pro—OpNP | 2, 4a | 96 | GPC | −33.0(D) |
| Cbo—D-Val—Pro—Arg(NO$_2$)-pNA | IV | III, Cbo—D-Val—OpNP | 2, 4a | 75 | GPC | +26.2(D) |
| Cbo—Pip—Arg(NO$_2$)-pNA | V | I, Cbo—Pip—OpNP | 2, 4a | 86 | GPC | −26.2(D) |
| Cbo—Val—Pip—Arg(NO$_2$)-pNA | VI | V, Cbo—D-Val—OpNP | 2, 4a | 23 | GPC | −24.0(D) |
| Cbo—Leu—Arg(NO$_2$)-pNA | VII | I, Cbo—Leu—OpNP | 2, 4a | 85 | GPC | +3.7(D) −33.4(M) |
| Boc—D-Ile—Leu—Arg(NO$_2$)-pNA | VIII | VII, tBoc—D-Ile—OH | 2, 4b | 94 | GPC | −2.5(M) |
| Cbo—D-Val—Leu—Arg(NO$_2$)-pNA | IX | VII, Cbo—D-Val—OpNP | 2, 4a | 64 | Cryst. (MeOH) | +1.7(D) |
| tBoc—Leu—Lys(Cbo)-pNA | X | II, tBoc—Leu—OpNP | 3, 4a | 74 | GPC | −4.7(D) |
| tBoc—D-Ile—Leu—Lys(Cbo)-pNA | XI | X, tBoc—D-Ile—OH | 3, 4b | 77 | GPC + Cryst. (MeOH) | −27.1(M) |
| Cbo—D-Val—Leu—Lys(Cbo)-pNA | XII | X, Cbo—D-Val—OpNP | 3, 4a | 90 | Cryst. (EtOH) | +17.1(D) |
| H—D-Val—Pro—Arg-pNA . 2HCl | XIII | IV (1.46 mmol) | 5 | 87 | GPC | −117(A) |
| H—D-Val—Pip—Arg-pNA . 2HCl | XIV | VI (0.20 mmol) | 5 | 85 | GPC | −81.5(A) |
| H—D-Ile—Leu—Arg-pNA . 2HCl | XV | VIII (0.38 mmol) | 5 | 75 | GPC | −58.2(A) |
| H—D-Val—Leu—Arg-pNA . 2HCl | XVI | IX (0.28 mmol) | 5 | 75 | GPC | −63.7(A) |
| H—D-Ile—Leu—Lys-pNA . 2HCl | XVII | XI (0.18 mmol) | 5 | 72 | GPC | −66.6(A) |
| H—D-Val—Leu—Lys-pNA . 2HCl | XVIII | XII (0.27 mmol) | 5 | 87 | GPC | −67.3(A) |
| Cbo—Ala—Arg(NO$_2$)-pNA | XIX | I, Cbo—Ala—OpNP | 2, 4a | 76 | Cryst. | +2.0(D) |
| Cbo—D-Ala—Ala—Arg(NO$_2$)-pNA | XX | XIX, Cbo—D-Ala—OpNP | 2, 4a | 80 | GPC | |
| Cbo—Gly—Arg(NO$_2$)-pNA | XXI | I, Cbo—Gly—OpNP | 2, 4a | 89 | Cryst. MeOH | −35.0(M) |
| Cbo—D-Leu—Gly—Arg(NO$_2$)-pNA | XXII | XXI, Cbo—D-Leu—OpNP | 2, 4a | 78 | GPC | |
| Cbo—Ile—Arg(NO$_2$)-pNA | XXIII | I, Cbo—Ile—OpNP | 2, 4a | 75 | GPC | +2.8(D) |
| Cbo—D-Leu—Ile—Arg(NO$_2$)-pNA | XXIV | XXIII, Cbo—D-Leu—OpNP | 2, 4a | 81 | GPC | |
| Cbo—Val—Arg(NO$_2$)-pNA | XXV | I, Cbo—Val—OpNP | 2, 4a | 84 | Cryst. MeOH | +4.9(D) |
| Cbo—D-Leu—Val—Arg(NO$_2$)-pNA | XXVI | XXV, Cbo—D-Leu—OpNP | 2, 4a | 79 | GPC | |
| Cbo—Aze—Arg(NO$_2$)-pNA | XXVII | I, Cbo—Aze—OpNP | 2, 4a | 69 | GPC | |
| Cbo—D-Val—Aze—Arg(NO$_2$)-pNA | XXVIII | XXVII, Cbo—D-Val—OpNP | 2, 4a | 73 | GPC | |
| Cbo—Phe—Arg(NO$_2$)-pNA | XXIX | I, Cbo—Phe—OpNP | 2, 4a | 80 | GPC | +5.7(D) |
| Cbo—D-Pro—Phe—Arg(NO$_2$)-pNA | XXX | XXIX, Cbo—D-Pro—OH | 2, 4b | 61 | GPC | |
| Cbo—D-Pip—Phe—Arg(NO$_2$)-pNA | XXXI | XXIX, Cbo—D-Pip—OpNP | 2, 4a | 57 | GPC | |
| Cbo—D-Leu—Leu—Arg(NO$_2$)-pNA | XXXII | VII, Cbo—D-Leu—OpNP | 2, 4a | 91 | GPC | |
| Boc—Phe—Lys(Cbo)-pNA | XXXIII | II, Boc—Phe—OpNP | 3, 4a | 65 | Cryst. EtOAc | |
| Cbo—D-Pro—Phe—Lys(Cbo)-pNA | XXXIV | XXXIII, Cbo—D-Pro—OH | 3, 4b | 62 | Cryst. MeOH | |
| H—D-Ala—Ala—Arg-pNA . 2HCl | XXXV | XX (0.5 mmol) | 5 | 87 | GPC | −42.0(A) |
| H—D-Leu—Gly—Arg-pNA . 2HCl | XXXVI | XXII (0.3 mmol) | 5 | 79 | GPC | −51.0(M) |
| H—D-Leu—Ile—Arg-pNA . 2HCl | XXXVII | XXIV (0.35 mmol) | 5 | 75 | GPC | −64.3(A) |
| H—D-Leu—Val—Arg-pNA . 2HCl | XXXVIII | XXVI (0.43 mmol) | 5 | 80 | GPC | −53.0(A) |
| H—D-Val—Aze—Arg-pNA . 2HCl | XXXIX | XXVIII (0.25 mmol) | 5 | 72 | GPC | −133(A) |
| H—D-Pro—Phe—Arg-pNA . 2HCl | XL | XXX (0.4 mmol) | 5 | 70 | GPC | −1.0(A) |
| H—D-Pip—Phe—Arg-pNA . 2HCl | XLI | XXXI (0.3 mmol) | 5 | 65 | GPC | −32.1(A) |
| H—D-Leu—Leu—Arg-pNA . 2HCl | XLII | XXXII (0.3 mmol) | 5 | 72 | GPC | −47.0(A) |
| H—D-Pro—Phe—Lys-pNA . 2HCl | XLIII | XXXIV (0.4 mmol) | 5 | 63 | GPC | −6.0(M) |

| Product | No. | TLC (R$_f$) | Cl$^-$-content found theor. |
|---|---|---|---|
| Cbo—Arg(NO$_2$)-pNA | I | P$_1$(0.34) | |
| tBoc—Lys(Cbo)-pNA | II | P$_1$(0.72) | |
| Cbo—Pro—Arg(NO$_2$)-pNA | III | p$_1$(0.28) | |
| Cbo—D-Val—Pro—Arg(NO$_2$)-pNA | IV | P$_1$(0.38) | |
| Cbo—Pip—Arg(NO$_2$)-pNA | V | P$_1$(0.30) | |
| Cbo—Val—Pip—Arg(NO$_2$)-pNA | VI | P$_1$(0.40) | |
| Cbo—Leu—Arg(NO$_2$)-pNA | VII | P$_1$(0.38) | |
| Boc—D-Ile—Leu—Arg(NO$_2$)-pNA | VIII | P$_1$(0.38) | |
| Cbo—D-Val—Leu—Arg(NO$_2$)-pNA | IX | P$_1$(0.42) | |
| tBoc—Leu—Lys(Cbo)-pNA | X | P$_\frac{1}{2}$(0.62) | |
| tBoc—D-Ile—Leu—Lys(Cbo)-pNA | XI | P$_1$(0.70) | |
| Cbo—D-Val—Leu—Lys(Cbo)-pNA | XII | P$_\frac{1}{2}$(0.68) | |
| H—D-Val—Pro—Arg-pNA . 2HCl | XIII | A(0.38) | 12.1(12.6) |
| H—D-Val—Pip—Arg-pNA . 2HCl | XIV | A(0.40) | 11.7(12.2) |
| H—D-Ile—Leu—Arg-pNA . 2HCl | XV | A(0.46) | 12.4(11.9) |
| H—D-Val—Leu—Arg-pNA . 2HCl | XVI | A(0.46) | 11.7(12.1) |
| H—D-Ile—Leu—Lys-pNA . 2HCl | XVII | A(0.44) | 13.0(12.5) |
| H—D-Val—Leu—Lys-pNA . 2HCl | XVIII | A(0.42) | 12.5(12.9) |
| Cbo—Ala—Arg(NO$_2$)-pNA | XIX | P$_1$(0.34) | |
| Cbo—D-Ala—Ala—Arg(NO$_2$)-pNA | XX | P$_1$ | |
| Cbo—Gly—Arg(NO$_2$)-pNA | XXI | P$_1$(0.12) | |
| Cbo—D-Leu—Gly—Arg(NO$_2$)-pNA | XXII | P$_1$(0.29) | |
| Cbo—Ile—Arg(NO$_2$)-pNA | XXIII | P$_1$(0.50) | |
| Cbo—D-Leu—Ile—Arg(NO$_2$)-pNA | XXIV | P$_1$(0.53) | |
| Cbo—Val—Arg(NO$_2$)-pNA | XXV | P$_1$(0.40) | |
| Cbo—D-Leu—Val—Arg(NO$_2$)-pNA | XXVI | P$_1$(0.65) | |
| Cbo—Aze—Arg(NO$_2$)-pNA | XXVII | P$_1$(0.47) | |

Table I-continued

| | | | |
|---|---|---|---|
| Cbo—D-Val—Aze—Arg(NO₂)-pNA | XXVIII | P₁(0.55) | |
| Cbo—Phe—Arg(NO₂)-pNA | XXIX | P₁(0.32) | |
| Cbo—D-Pro—Phe—Arg(NO₂)-pNA | XXX | P₁(0.36) | |
| Cbo—D-Pip—Phe—Arg(NO₂)-pNA | XXXI | P₁(0.38) | |
| Cbo—D-Leu—Leu—Arg(NO₂)-pNA | XXXII | P₁(0.37) | |
| Boc—Phe—Lys(Cbo)-pNA | XXXIII | P₁(0.78) | |
| Cbo—D-Pro—Phe—Lys(Cbo)-pNA | XXXIV | P₁(0.78) | |
| H—D-Ala—Ala—Arg-pNA . 2HCl | XXXV | A(0.44) | 13.2(13.8) |
| H—D-Leu—Gly—Arg-pNA . 2HCl | XXXVI | A(0.44) | 13.0(13.1) |
| H—D-Leu—Ile—Arg-pNA . 2HCl | XXXVII | A(0.46) | 12.3(11.9) |
| H—D-Leu—Val—Arg-pNA . 2HCl | XXXVIII | A(0.46) | 11.6(12.1) |
| H—D-Val—Aze—Arg-pNA . 2HCl | XXXIX | A(0.42) | 12.2(12.9) |
| H—D-Pro—Phe—Arg-pNA . 2HCl | XL | A(0.40) | 10.9(11.6) |
| H—D-Pip—Phe—Arg-pNA . 2HCl | XLI | A(0.44) | 11.0(11.3) |
| H—D-Leu—Leu—Arg-pNA . 2HCl | XLII | A(0.47) | 11.6(12.0) |
| H—D-Pro—Phe—Lys-pNA . 2HCl | XLIII | A(0.50) | 12.1(12.1) |

ˣData for the determination of $[\alpha]_D^{24}$: C = 0.5–1.0; solvent: (D) = DMF, (M) = MeOH, (A) = 50% AcOH (aq)

Table II

| Substrate | | Solubility mg/ml bufferˣ | Rel T | Reaction rates | | | UK |
|---|---|---|---|---|---|---|---|
| | | | | Try | Pl | Kal | |
| Bz—Val—Pro—Arg-pNA | | 0.3 | 6 | 60 | | | 15 |
| H—Val—Pro—Arg-pNA | | 40 | 6 | 55 | | | 15 |
| H—D-Val—Pro—Arg-pNA | (XIII) | 100 | 80 | 100 | | | 95 |
| Bz—Val—Pip—Arg-pNA | | | 4 | 45 | | | 30 |
| H—Val—Pip—Arg-pNA | | | 4 | 35 | | | 45 |
| H—D-Val—Pip—Arg-pNA | (XIV) | | 100 | 70 | | | 100 |
| Bz—Val—Leu—Arg-pNA | | 0.2 | | | | 100 | |
| H—Val—Leu—Arg-pNA | | | | | | 50 | |
| H—D-Val—Leu—Arg-pNA | (XVI) | 600 | | | | 100 | |
| Bz—Val—Leu—Lys-pNA | | 0.5 | | | 100 | | |
| H—Val—Leu—Lys-pNA | | | | | 25 | | |
| H—D-Val—Leu—Lys-pNA | (XVIII) | >100 | | | 100 | | |
| Bz—Ile—Leu—Arg-pNA | | 0.2 | | 55 | | 100 | |
| H—Ile—Leu—Arg-pNA | | | | 10 | | 20 | |
| H—D-Ile—Leu—Arg-pNA | (XV) | 4 | | 75 | | 100 | |
| Bz—Ile—Leu—Lys-pNA | | 1 | | 130 | | | |
| H—Ile—Leu—Lys-pNA | | | | 35 | | | |
| H—D-Ile—Leu—Lys-pNA | (XVII) | 20 | | 100 | | | |

ˣBuffer = Tris, pH 8.2, I 0.15

In the table above the relative reaction rates for the different substrates are stated in relation to a reference substrate chosen for each enzyme. Symbols, reference substrates and their sensitivity for the respective enzymes are according to the following:

| Enzyme (symbol) | Ref. substrate No. | Sensitivity (stated amount of enzyme gives the activity 0.1 nkat) $\Delta$OD/min = 0.0254 |
|---|---|---|
| Thrombin (T) | XIV | 0.06 INH |
| Trypsin (Try) | XIII | 0.03 µg (Novo) |
| Plasmin (Pl) | XVIII | 0.01 CU |
| Kallikrein (Kal) | XVI | 0.2 BE |
| Urokinase (UK) | XIV | 40 Ploug E |

We claim:

1. A method for the quantitative determination of serine proteases which comprises contacting the substrate for which said determination is desired with a diagnostically active chromogenic substrate with good solubility and a high specificity to serine proteases, having the following general formula:

$$H—D—A_1—A_2—A_3—NH—R$$

or salts thereof, wherein $A_1$ is an amino acid selected from the group consisting of Gly, Ala, Val, Leu, Ile, Pip, Pro, and Aze; $A_2$ is an amino acid selected from the group consisting of Gly, Ala, Val, Leu, Ile, Pip, Pro, Aze, and Phe; $A_3$ is an amino acid selected from the group consisting of Arg, Lys, and Orn; and R is a chromophoric group, and then spectrophotometrically measuring the degree of enzymatic hydrolysis.

2. The method of claim 1 wherein R is nitrophenyl, naphthyl, nitronaphthyl, methoxynaphthyl, quinolyl or nitroquinolyl.

3. The method of claim 1 wherein R is nitrophenyl.

4. The method of claim 3 wherein said spectrometrically measuring is carried out at 405 nm.

5. The method of claim 1 wherein said substrate is H-D-Val-Pro-Arg-pNA, or salt thereof.

6. The method of claim 1 wherein said substrate is H-D-Val-Pip-Arg-pNA, or salt thereof.

7. The method of claim 1 wherein said substrate is H-D-Val-Leu-Arg-pNA, or salt thereof.

8. The method of claim 1 wherein said substrate is H-D-Val-Leu-Lys-pNA, or salt thereof.

9. The method of claim 1 wherein said substrate is H-D-Ile-Leu-Arg-pNA, or salt thereof.

10. The method of claim 1 wherein said substrate is H-D-Ile-Leu-Lys-pNA, or salt thereof.

11. The method of claim 1 wherein said substrate is H-D-Pro-Phe-Arg-pNA, or salt thereof.

12. The method of claim 1 wherein said substrate is H-D-Val-Pip-Arg-pNA, or salt thereof.

13. The method of claim 1 wherein said substrate is H-D-Pro-Phe-Lys-pNA, or salt thereof.

14. The method of claim 1 wherein said substrate is H-D-Ala-Ala-Arg-pNA, or salt thereof.

15. The method of claim 1 wherein said substrate is H-D-Leu-Gly-Arg-pNA, or salt thereof.
16. The method of claim 1 wherein said substrate is H-D-Leu-Ile-Arg-pNA, or salt thereof.
17. The method of claim 1 wherein said substrate is H-D-Leu-Val-Arg-pNA, or salt thereof.
18. The method of claim 1 wherein said substrate is H-D-Leu-Val-Lys-pNA, or salt thereof.
19. The method of claim 1 wherein said substrate is H-D-Pip-Phe-Arg-pNA, or salt thereof.
20. The method of claim 1 wherein said substrate is H-D-Leu-Leu-Arg-pNA, or salt thereof.
21. The method of claim 1 wherein $A_1$ is Val.
22. The method of claim 1 wherein $A_1$ is Ile.
23. The method of claim 1 wherein $A_1$ is Pro.
24. The method of claim 1 wherein $A_2$ is Pro.
25. The method of claim 1 wherein $A_2$ is Pip.
26. The method of claim 1 wherein $A_2$ is Leu.
27. The method of claim 1 wherein $A_2$ is Phe.
28. The method of claim 1 wherein $A_3$ is Arg.
29. The method of claim 1 wherein $A_3$ is Lys.
30. The method of claim 1 which is a hydrochloride salt.
31. The method of claim 1 wherein said spectrophotometrically measuring is carried out at 405 nm.

* * * * *